US012616765B2

(12) United States Patent
Fellner et al.

(10) Patent No.: US 12,616,765 B2
(45) Date of Patent: May 5, 2026

(54) UV INTEGRATED DISINFECTING CAP

(71) Applicant: Bard Access Systems, Inc., Salt Lake City, UT (US)

(72) Inventors: Stefan Josef Fellner, Salt Lake City, UT (US); Steffan Sowards, Salt Lake City, UT (US); William Robert McLaughlin, Bountiful, UT (US); Dustin Payne, West Jordan, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 572 days.

(21) Appl. No.: 18/095,469

(22) Filed: Jan. 10, 2023

(65) Prior Publication Data

US 2024/0226352 A1 Jul. 11, 2024

(51) Int. Cl.
| | |
|---|---|
| *A61L 2/10* | (2006.01) |
| *A61L 2/26* | (2006.01) |
| *A61M 39/16* | (2006.01) |
| *A61M 39/20* | (2006.01) |

(52) U.S. Cl.
CPC ................................... *A61L 2/10* (2013.01); *A61L 2/26* (2013.01); *A61M 39/16* (2013.01); *A61M 39/20* (2013.01); *A61L 2202/11* (2013.01); *A61L 2202/123* (2013.01); *A61L 2202/16* (2013.01); *A61L 2202/24* (2013.01)

(58) Field of Classification Search
CPC .......... A61L 2/10; A61L 2/26; A61L 2202/11; A61L 2202/123; A61L 2202/16; A61L 2202/24; A61L 2/24; A61L 2202/14; A61M 39/16; A61M 39/20; A61M 25/00; A61M 2025/0019; A61M 39/18; A61M 2039/167
See application file for complete search history.

(56) References Cited

U.S. PATENT DOCUMENTS

| | | | |
|---|---|---|---|
| 5,225,172 | A | 7/1993 | Meyler et al. |
| 5,441,504 | A | 8/1995 | Pohndorf et al. |
| 6,811,563 | B2 | 11/2004 | Savage, Jr. et al. |
| 6,908,460 | B2 | 6/2005 | DiStefano |
| 7,210,817 | B2 | 5/2007 | Lee et al. |
| 7,274,844 | B2 | 9/2007 | Walt et al. |

(Continued)

FOREIGN PATENT DOCUMENTS

| | | |
|---|---|---|
| CA | 2199384 C | 6/2006 |
| CA | 3080966 A1 | 11/2020 |

(Continued)

OTHER PUBLICATIONS

Cabral, João, and Rodrigues A. G. "Blue light disinfection in hospital infection control: advantages, drawbacks, and pitfalls." Antibiotics 8.2 (2019): 58.

(Continued)

*Primary Examiner* — Theodore J Stigell
(74) *Attorney, Agent, or Firm* — Rutan & Tucker LLP

(57) ABSTRACT
A disinfecting device having a housing and an ultraviolet source located in the housing. The disinfecting device may include a tube that includes a first end connected to the housing and a second end free of the housing. An end cap may be located at the second end of the tube. In use, ultraviolet light may be emitted from the ultraviolet source and propagated to the end cap in order to disinfect a portion of a medical device.

20 Claims, 7 Drawing Sheets

(56) References Cited

U.S. PATENT DOCUMENTS

| | | | |
|---|---|---|---|
| 8,197,087 | B2 | 6/2012 | Sobue et al. |
| 8,246,666 | B2 | 8/2012 | Pressler et al. |
| 8,372,128 | B2 | 2/2013 | Reuben |
| 8,387,405 | B2 | 3/2013 | Johnson |
| 8,556,950 | B2 | 10/2013 | Rioux et al. |
| 9,592,374 | B2 | 3/2017 | Muse |
| 9,604,072 | B2 | 3/2017 | Brezinski |
| 9,925,285 | B1 | 3/2018 | Zaborsky et al. |
| 9,981,052 | B2 | 5/2018 | Clynne et al. |
| 10,603,393 | B2 | 3/2020 | Rioux et al. |
| 10,639,389 | B2 | 5/2020 | Paul et al. |
| 2002/0081228 | A1 | 6/2002 | Hui et al. |
| 2003/0018373 | A1 | 1/2003 | Eckhardt et al. |
| 2003/0036735 | A1* | 2/2003 | Jepson ............... A61M 39/045 251/149.3 |
| 2003/0063997 | A1 | 4/2003 | Fryer et al. |
| 2005/0101854 | A1 | 5/2005 | Larson et al. |
| 2007/0123825 | A1 | 5/2007 | King et al. |
| 2008/0027399 | A1 | 1/2008 | Harding et al. |
| 2008/0257355 | A1 | 10/2008 | Rao et al. |
| 2008/0283769 | A1 | 11/2008 | Deshays |
| 2009/0177163 | A1 | 7/2009 | King et al. |
| 2010/0296971 | A1 | 11/2010 | Gaska et al. |
| 2011/0144566 | A1 | 6/2011 | Dacey, Jr. et al. |
| 2012/0053512 | A1 | 3/2012 | Muse |
| 2012/0116294 | A1 | 5/2012 | Boenig et al. |
| 2012/0143138 | A1 | 6/2012 | King et al. |
| 2012/0161032 | A1 | 6/2012 | Arcand et al. |
| 2012/0321509 | A1 | 12/2012 | Bak |
| 2013/0303996 | A1 | 11/2013 | Rasooly et al. |
| 2013/0323119 | A1* | 12/2013 | Alwan ....................... A61L 2/10 250/455.11 |
| 2013/0323120 | A1* | 12/2013 | Ma ............................ A61L 2/28 250/455.11 |
| 2014/0217307 | A1 | 8/2014 | Messina et al. |
| 2014/0257186 | A1 | 9/2014 | Kerr |
| 2015/0080851 | A1 | 3/2015 | Kurth et al. |
| 2015/0148734 | A1 | 5/2015 | Fewkes et al. |
| 2015/0157209 | A1 | 6/2015 | Dantus |
| 2015/0165185 | A1 | 6/2015 | Cohen et al. |
| 2015/0217010 | A1 | 8/2015 | Whitney |
| 2015/0231287 | A1 | 8/2015 | Lin et al. |
| 2015/0238747 | A1* | 8/2015 | Russo ................ A61M 39/1011 604/533 |
| 2015/0245810 | A1 | 9/2015 | Shine et al. |
| 2015/0273093 | A1 | 10/2015 | Holub et al. |
| 2015/0283277 | A1 | 10/2015 | Schafer et al. |
| 2016/0038621 | A1* | 2/2016 | Victor .................. A61N 5/0601 128/202.16 |
| 2016/0128526 | A1 | 5/2016 | Dobrinsky et al. |
| 2016/0151639 | A1 | 6/2016 | Scharf et al. |
| 2016/0303265 | A1 | 10/2016 | Coles |
| 2016/0310077 | A1 | 10/2016 | Hunter et al. |
| 2016/0317687 | A1 | 11/2016 | Dayton |
| 2017/0136209 | A1 | 5/2017 | Burnett et al. |
| 2017/0196478 | A1 | 7/2017 | Hunter |
| 2017/0232123 | A1 | 8/2017 | Burapachaisri et al. |
| 2017/0252550 | A1 | 9/2017 | Wegener et al. |
| 2017/0281812 | A1 | 10/2017 | Dobrinsky et al. |
| 2017/0296142 | A1 | 10/2017 | Wodecki et al. |
| 2018/0280616 | A1 | 10/2018 | Witt et al. |
| 2018/0369560 | A1 | 12/2018 | Ball et al. |
| 2019/0111240 | A1 | 4/2019 | Fia et al. |
| 2019/0151587 | A1 | 5/2019 | Vazales et al. |
| 2019/0192872 | A1 | 6/2019 | Schwarz et al. |
| 2019/0290360 | A1 | 9/2019 | Goodrich et al. |
| 2019/0290791 | A1* | 9/2019 | Baker .................... A61B 90/70 |
| 2019/0374668 | A1 | 12/2019 | Kopperschmidt et al. |
| 2020/0030473 | A1 | 1/2020 | Sugimoto et al. |
| 2020/0147248 | A1 | 5/2020 | Mintie et al. |
| 2020/0188543 | A1 | 6/2020 | Etter et al. |
| 2020/0261610 | A1 | 8/2020 | Rioux et al. |
| 2020/0324078 | A1 | 10/2020 | Motley et al. |
| 2020/0360549 | A1 | 11/2020 | Neveu et al. |
| 2020/0368379 | A1 | 11/2020 | Agarwal |
| 2021/0113725 | A1 | 4/2021 | Etter et al. |
| 2021/0154342 | A1 | 5/2021 | Canfield |
| 2021/0162081 | A1 | 6/2021 | Zhang et al. |
| 2021/0204818 | A1 | 7/2021 | Akins et al. |
| 2021/0236859 | A1 | 8/2021 | Park et al. |
| 2021/0338879 | A1 | 11/2021 | Davis et al. |
| 2022/0016439 | A1 | 1/2022 | Shah et al. |
| 2022/0096677 | A1 | 3/2022 | Chan et al. |
| 2022/0152243 | A1 | 5/2022 | Koppen et al. |
| 2022/0203007 | A1 | 6/2022 | Yuds et al. |
| 2022/0273837 | A1 | 9/2022 | Paul et al. |
| 2022/0313851 | A1 | 10/2022 | Subramanya et al. |
| 2022/0347456 | A1 | 11/2022 | Messerly |
| 2022/0387643 | A1 | 12/2022 | Baarman |
| 2023/0089985 | A1 | 3/2023 | Li et al. |
| 2023/0118324 | A1 | 4/2023 | Hong et al. |
| 2023/0233716 | A1 | 7/2023 | Yoon et al. |
| 2023/0293741 | A1 | 9/2023 | Matsui et al. |
| 2023/0301626 | A1 | 9/2023 | Howell |
| 2024/0115749 | A1 | 4/2024 | Payne et al. |
| 2024/0188859 | A1 | 6/2024 | Fellner et al. |
| 2024/0189467 | A1 | 6/2024 | Urry et al. |
| 2024/0226350 | A1 | 7/2024 | Payne et al. |
| 2024/0226351 | A1 | 7/2024 | Payne et al. |
| 2024/0252789 | A1 | 8/2024 | Hayden et al. |
| 2024/0335636 | A1 | 10/2024 | Laine et al. |
| 2024/0342325 | A1 | 10/2024 | Urry et al. |
| 2024/0350688 | A1 | 10/2024 | Prince |
| 2024/0374770 | A1 | 11/2024 | Durfee |
| 2025/0073360 | A1 | 3/2025 | Payne et al. |

FOREIGN PATENT DOCUMENTS

| | | |
|---|---|---|
| CN | 104873219 A | 9/2015 |
| CN | 106308727 A | 1/2017 |
| CN | 208481489 U | 2/2019 |
| CN | 209790441 U | 12/2019 |
| CN | 213373944 U | 6/2021 |
| CN | 213551294 U | 6/2021 |
| CN | 113101207 A | 7/2021 |
| CN | 213642120 U | 7/2021 |
| CN | 113476076 A | 10/2021 |
| CN | 215426269 U | 1/2022 |
| EP | 3195805 A1 | 7/2017 |
| EP | 3738617 A2 | 11/2020 |
| JP | 2005198761 A | 7/2005 |
| KR | 20140003473 U | 6/2014 |
| KR | 101654328 B1 | 9/2016 |
| KR | 20220000634 U | 3/2022 |
| KR | 20220063891 A | 5/2022 |
| KR | 102452057 B1 | 10/2022 |
| WO | 9607451 A2 | 3/1996 |
| WO | 2011068545 A1 | 6/2011 |
| WO | 2013134421 A1 | 9/2013 |
| WO | 2014165854 A1 | 10/2014 |
| WO | 2015157518 A1 | 10/2015 |
| WO | 2019108431 A1 | 6/2019 |
| WO | 2020115230 A1 | 6/2020 |
| WO | 2021146701 A1 | 7/2021 |
| WO | 2021157769 A1 | 8/2021 |
| WO | 2022036886 A1 | 2/2022 |
| WO | 2022046138 A1 | 3/2022 |
| WO | 2022200038 A2 | 9/2022 |
| WO | 2022232479 A1 | 11/2022 |
| WO | 2023183426 A1 | 9/2023 |
| WO | 2024081335 A1 | 4/2024 |
| WO | 2024124112 A1 | 6/2024 |
| WO | 2024129817 A1 | 6/2024 |
| WO | 2024/151420 A1 | 7/2024 |
| WO | 2024/151421 A1 | 7/2024 |
| WO | 2024/151648 A1 | 7/2024 |
| WO | 2024163670 A1 | 8/2024 |
| WO | 2024211387 A1 | 10/2024 |
| WO | 2024215932 A1 | 10/2024 |
| WO | 2024220523 A1 | 10/2024 |

(56) References Cited

FOREIGN PATENT DOCUMENTS

WO          2024233805 A1    11/2024
WO          2025049496 A1    3/2025

OTHER PUBLICATIONS

Changtong, Chuchawin, et al. "A porphyrin molecule that generates, traps, stores, and releases singlet oxygen." Journal of Photochemistry and Photobiology A: Chemistry 260 (2013): 9-13.

Halstead, Fenella D., et al. "The potential of visible blue light (405 nm) as a novel decontamination strategy for carbapenemase-producing enterobacteriaceae (CPE)." Antimicrobial Resistance & Infection Control 8.1 (2019): 1-8.

Tsen, Shaw-Wei David, et al. "Inactivation of multidrug-resistant bacteria and bacterial spores and generation of high-potency bacterial vaccines using ultrashort pulsed lasers." Journal of Biophotonics 15.2 (2022): e202100207.

PCT/US2023/015961 filed Mar. 22, 2023, International Search Report and Written Opinion dated Jul. 17, 2023.

PCT/US2023/034981 filed Oct. 11, 2023, International Search Report and Written Opinion dated Dec. 11, 2023.

PCT/US2024/024136 filed Apr. 11, 2024, International Search Report and Written Opinion dated Sep. 18, 2024.

PCT/US2024/024969 filed Apr. 17, 2024, International Search Report and Written Opinion dated Sep. 27, 2024.

PCT/US2024/028630 filed May 9, 2024, International Search Report and Written Opinion dated Sep. 18, 2024.

PCT/US2024/044069 filed Aug. 27, 2024, International Search Report and Written Opinion dated Jan. 31, 2025.

U.S. Appl. No. 17/732,614, filed Apr. 29, 2022 Non-Final Office Action dated May 9, 2025.

U.S. Appl. No. 17/963,594, filed Oct. 11, 2022 Restriction Requirement dated Jun. 3, 2025.

U.S. Appl. No. 18/125,029, filed Mar. 22, 2023 Notice of Allowance dated Dec. 18, 2024.

PCT/US2023/083767 filed Dec. 13, 2023, International Search Report and Written Opinion dated Apr. 25, 2024.

PCT/US2023/085837 filed Dec. 22, 2023, International Search Report and Written Opinion dated Apr. 9, 2024.

PCT/US2024/010902 filed Jan. 9, 2024, International Search Report and Written Opinion dated Apr. 24, 2024.

PCT/US2023/083089 filed Dec. 8, 2023, International Search Report and Written Opinion dated Jun. 3, 2024.

PCT/US2023/085839 filed Dec. 22, 2023, International Search Report and Written Opinion dated Jun. 11, 2024.

PCT/US2024/013858 filed Jan. 31, 2024, International Search Report and Written Opinion dated May 22, 2024.

Changtong et al., "A porphyrin molecule that generates, traps, stores, and releases singlet oxygen.", Journal of Photochemistry and Photobiology A: Chemistry 260 (Sep. 13, 2013).

PCT/US2022/026888 filed Apr. 29, 2022 International Search Report and Writtent Opinion dated Jul. 29, 2022.

Tsen et al., "Inactivation of multidrug-resistant bacteria and bacterial spores and generation of high-potency bacterial vaccines using ultrashort pulsed lasers." Journal of Biophotonics, 2021.

CS Medical "Caring for TEE Probes the Right Way" Mar. 17, 2022.

PCT/US2023/085837 filed Dec. 22, 2023, International Preliminary Report on Patentability dated Jul. 3, 2025.

PCT/US2024/013858 filed Jan. 31, 2024 International Preliminary Report on Patentability dated Jul. 31, 2025.

PCT/US2024/022801 filed Apr. 4, 2024, International Search Report and Written Opinion dated Sep. 6, 2024.

U.S. Appl. No. 17/732,614, filed Apr. 29, 2022 Advisory Action Nov. 14, 2025.

U.S. Appl. No. 17/732,614, filed Apr. 29, 2022 Final Office Action dated Sep. 4, 2025.

U.S. Appl. No. 17/963,594, filed Oct. 11, 2022 Non-Final Office Action dated Aug. 22, 2025.

U.S. Appl. No. 18/077,994, filed Dec. 8, 2022 Non-Final Office Action dated Jul. 30, 2025.

U.S. Appl. No. 18/080,624, filed Dec. 13, 2022 Non-Final Office Action dated Oct. 1, 2025.

U.S. Appl. No. 18/080,624, filed Dec. 13, 2022 Restriction Requirement dated Jul. 10, 2025.

U.S. Appl. No. 18/094,760, filed Jan. 9, 2023 Non-Final Office Action dated Sep. 10, 2025.

U.S. Appl. No. 18/094,760, filed Jan. 9, 2023 Restriction Requirement dated Jun. 18, 2025.

U.S. Appl. No. 18/094,785, filed Jan. 9, 2023 Non-Final Office Action dated Aug. 27, 2025.

U.S. Appl. No. 18/094,785, filed Jan. 9, 2023 Restriction Requirement dated Jun. 18, 2025.

U.S. Appl. No. 18/104,448, filed Feb. 1, 2023 Non-Final Office Action dated Oct. 30, 2025.

U.S. Appl. No. 18/132,261, filed Apr. 7, 2023 Restriction Requirement dated Nov. 10, 2025.

U.S. Appl. No. 18/195,018, filed May 9, 2023 Final Office Action dated Oct. 23, 2025.

U.S. Appl. No. 18/195,018, filed May 9, 2023 Non-Final Office Action dated Jul. 3, 2025.

U.S. Appl. No. 17/732,614, filed Apr. 29, 2022 Non-Final Office Action dated Jan. 28, 2026.

U.S. Appl. No. 17/963,594, filed Oct. 11, 2022 Advisory Action dated Mar. 6, 2026.

U.S. Appl. No. 17/963,594, filed Oct. 11, 2022 Final Office Action dated Jan. 8, 2026.

U.S. Appl. No. 18/077,994, filed Dec. 8, 2022 Final Office Action dated Feb. 12, 2026.

U.S. Appl. No. 18/080,624, filed Dec. 13, 2022 Final Office Action dated Jan. 30, 2026.

U.S. Appl. No. 18/104,448, filed Feb. 1, 2023 Final Office Action dated Februray 25, 2026.

U.S. Appl. No. 18/132,261, filed Apr. 7, 2023 Non-Final Office Action dated Feb. 9, 2026.

US 18/136, 111 filed Apr. 18, 2023 Notice of Allowance dated Dec. 23, 2025.

U.S. Appl. No. 18/239,048, filed Aug. 28, 2023 Restriction Requirement dated Mar. 3, 2026.

* cited by examiner 502
500
506
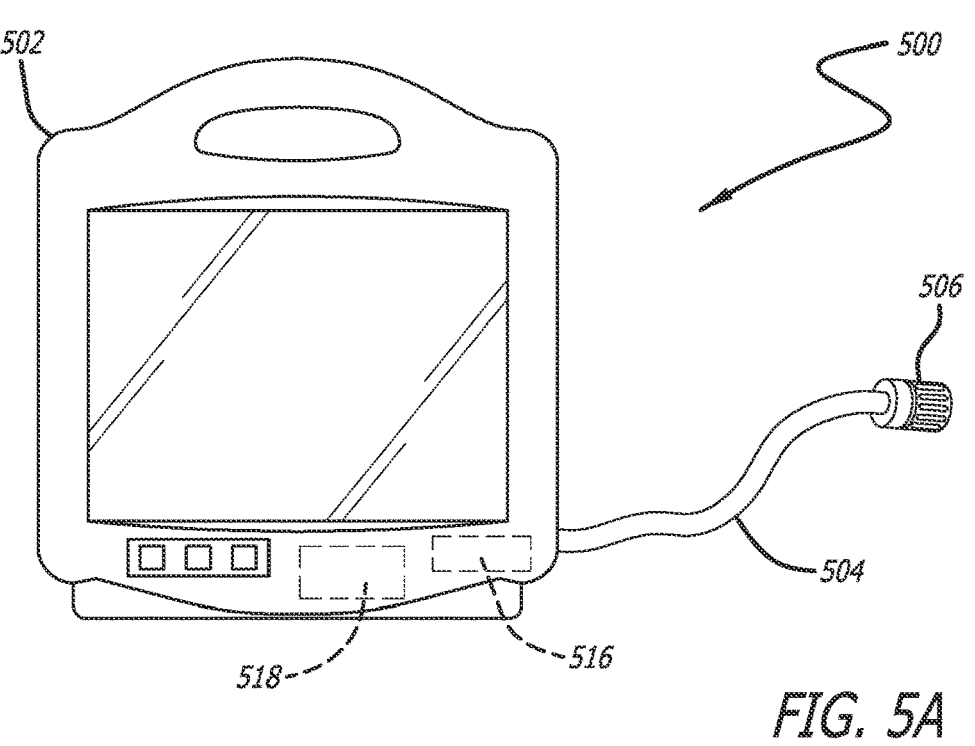
504
518          516
*FIG. 5A*
500
510
506
508
504
509
*FIG. 5B*
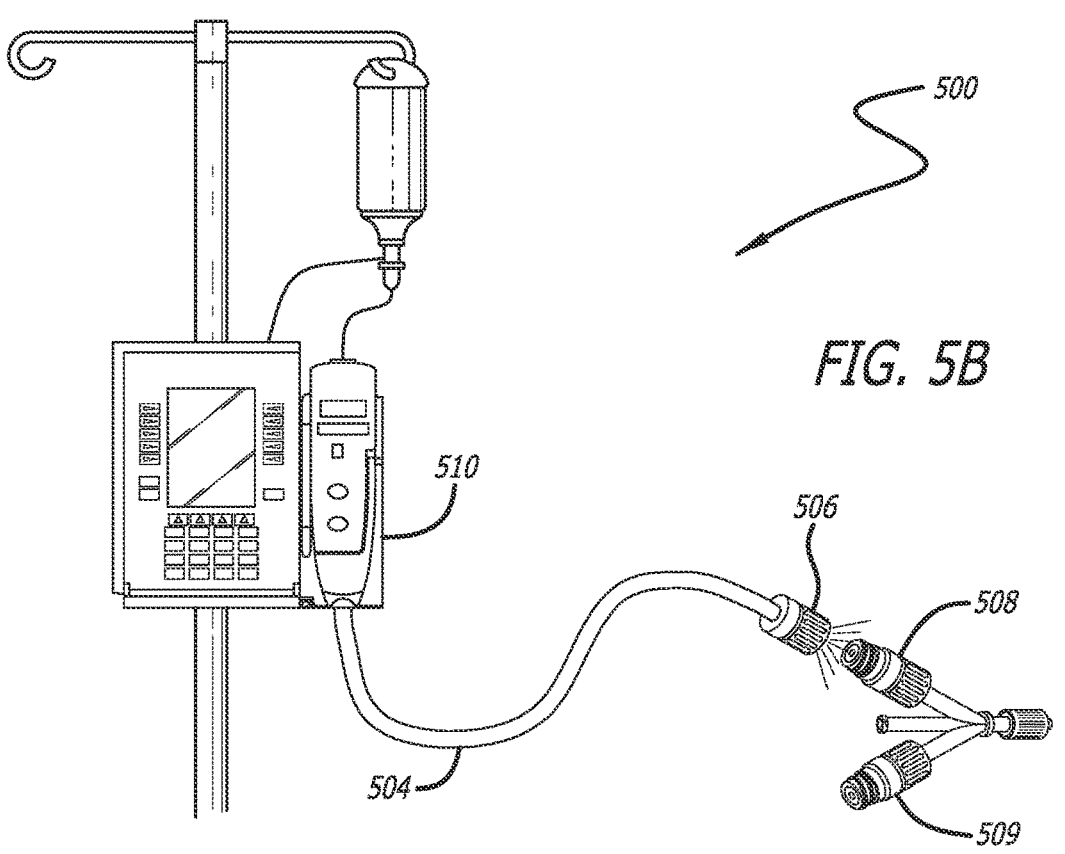

UV INTEGRATED DISINFECTING CAP

BACKGROUND

One challenge of modern medical treatment is control of infection and the spread of microbial organisms. One area where this challenge is constantly presented is in infusion therapy procedures. Infusion therapy is one of the most common health care procedures. Hospitalized, home care, and other patients receive fluids, pharmaceuticals, and blood products via a vascular access device inserted into the vascular system. Infusion therapy may be used to treat an infection, provide anesthesia or analgesia, provide nutritional support, treat cancerous growths, and maintain blood pressure and heart rhythm, or many other clinically significant uses.

In some instances, an implanted port may be placed under a patient's skin to enable intravenous (IV) treatments and transfusions directly into a vein. As convenient as implanted ports are, the spread of microbial organisms into the patient's vein through the implanted port is of great concern. Similar concerns exist with connectors of other medical apparatuses as well such as connectors at proximal or distal ends of a catheter. Thus, what is needed is a method, system, and apparatus for disinfecting medical apparatuses thereby preventing the spread of microbial organisms into the patient body.

SUMMARY

Briefly summarized, embodiments of the present invention are directed to a disinfecting device, that may include a housing, an ultraviolet source located in the housing, a tube that includes a first end connected to the housing and a second end free of the housing, and an end cap located at the second end of the tube, wherein ultraviolet light is emitted from the ultraviolet source and propagated to the end cap.

In some aspects, the tube or the end cap may include a coating to encourage propagation of the ultraviolet light. In some aspects, the coating may be positioned on an inner surface of the tube or the end cap.

In some aspects, the coating may be positioned on an outer surface of the tube or the end cap. In some aspects, the tube or end cap may include one or more fiber configured to transmit the ultraviolet light. In some aspects, the one or more fiber may be embedded in a wall of the tube or the end cap. In some aspects, the ultraviolet source may include one or more light emitting diodes (LEDs) or superluminescent diodes (SLEDs).

In some aspects, the housing may be configured to be held in a hand of a user. In some aspects, the housing may be configured to be worn by a user (e.g., on an extremity such as an arm or leg). In some aspects, the disinfecting device may include a pump located within the housing. In some aspects, the pump may be an infusion pump. In some aspects, the end cap may be configured to attached to a medical device.

In some aspects, the medical device is one or more hub, catheter, and port. In some aspects, the end cap may be a Luer connector. In some aspects, the end cap may be a barbed port. In some aspects, the end cap may include a friction fit connection.

In some aspects, the disinfecting device may include a power source configured for providing power to the ultraviolet source. In some aspects, the power source may be one or more battery, capacitor, and inductance coil. In some aspects, the disinfecting device may include a transmitter or transceiver. In some aspects, the transmitter or transceiver may include an RFID or wireless communication enabled transmitter or transceiver.

These and other features of embodiments of the present invention will become more fully apparent from the following description and appended claims or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 5A illustrates a disinfection device forming a part of a medical device or network in accordance with an embodiment;

FIG. 5B illustrates a disinfection device forming a part of an infusion pump in accordance with an embodiment;

DETAILED DESCRIPTION

Figure 1:
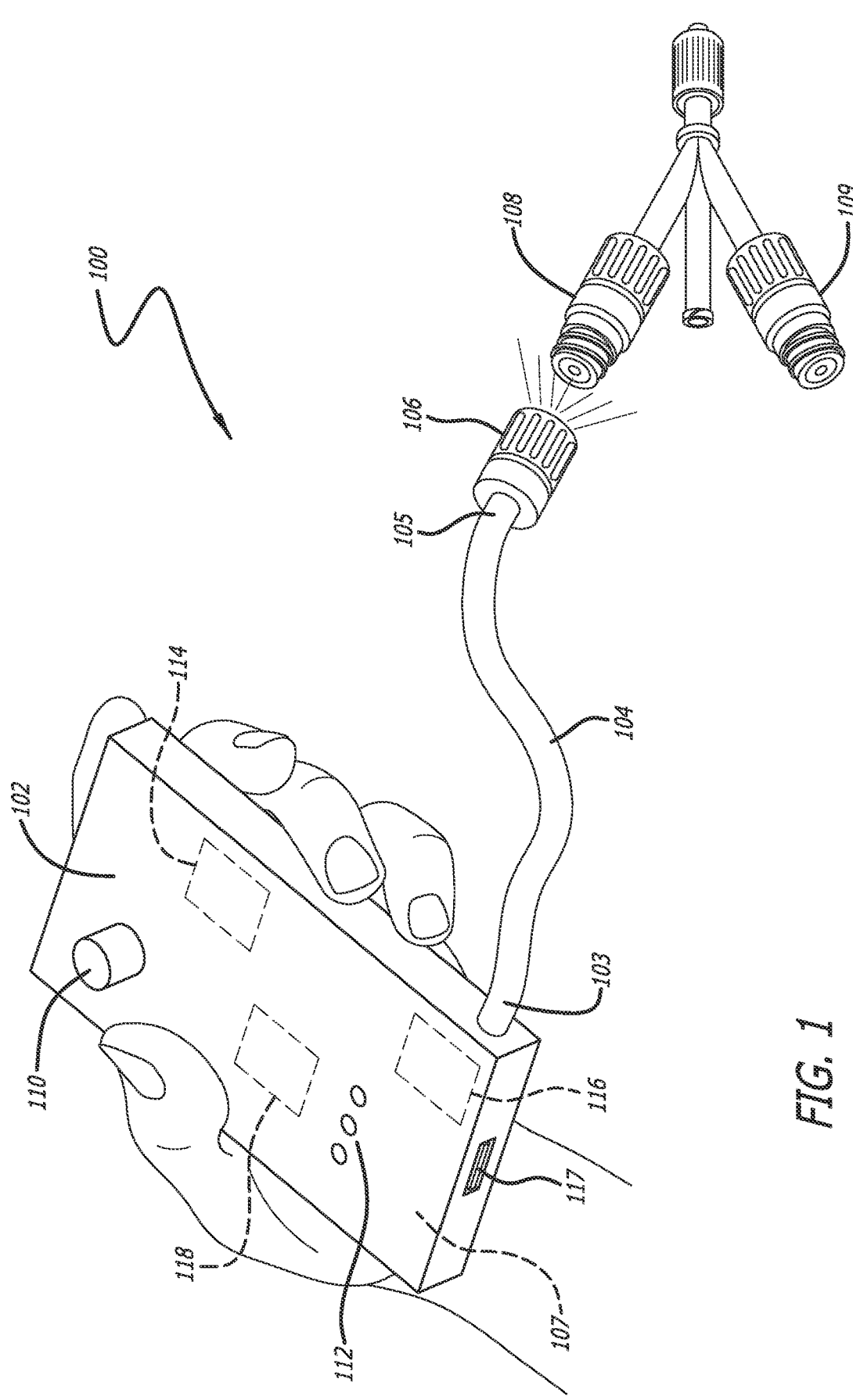
FIG. 1 illustrates a handheld disinfection device connected to a hub requiring disinfection in accordance with an embodiment.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a widget disclosed herein includes a portion of the widget intended to be near a user (e.g., a holder of the widget). Likewise, a "proximal length" of, for example, the widget includes a length of the widget intended to be near the user. A "proximal end" of, for example, the widget includes an end of the widget intended to be near the user. The proximal portion, the proximal end portion, or the proximal length of the widget can include the proximal end of the widget; however, the proximal portion, the proximal end portion, or the proximal length of the widget need not include the proximal end of the widget. That is, unless context suggests otherwise, the proximal portion, the proximal end portion, or the proximal length of the widget is not a terminal portion or terminal length of the widget.

With respect to "distal," a "distal portion" or a "distal end portion" of, for example, a widget disclosed herein includes a portion of the widget intended to be opposite the user with respect to the proximal portion (e.g., "away" from the user). Likewise, a "distal length" of, for example, the widget includes a length of the widget intended to be opposite the proximal portion and away from the user. A "distal end" of, for example, the widget includes an end of the widget intended to be opposite the proximal end. The distal portion, the distal end portion, or the distal length of the widget can include the distal end of the widget; however, the distal portion, the distal end portion, or the distal length of the widget need not include the distal end of the widget. That is, unless context suggests otherwise, the distal portion, the distal end portion, or the distal length of the widget is not a terminal portion or terminal length of the widget.

The term "logic" may be representative of hardware, firmware or software that is configured to perform one or more functions. As hardware, the term logic may refer to or include circuitry having data processing and/or storage functionality. Examples of such circuitry may include, but are not limited or restricted to, a hardware processor (e.g., microprocessor, one or more processor cores, a digital signal processor, a programmable gate array, a microcontroller, an application specific integrated circuit "ASIC", etc.), a semiconductor memory, or combinatorial elements.

Additionally, or in the alternative, the term logic may refer to or include software such as one or more processes, one or more instances, Application Programming Interface(s) (API), subroutine(s), function(s), applet(s), servlet(s), routine(s), source code, object code, shared library/dynamic link library (dll), or even one or more instructions. This software may be stored in any type of a suitable non-transitory storage medium, or transitory storage medium (e.g., electrical, optical, acoustical, or other form of propagated signals such as carrier waves, infrared signals, or digital signals). Examples of a non-transitory storage medium may include, but are not limited or restricted to, a programmable circuit; non-persistent storage such as volatile memory (e.g., any type of random access memory "RAM"); or persistent storage such as non-volatile memory (e.g., read-only memory "ROM", power-backed RAM, flash memory, phase-change memory, etc.), a solid-state drive, hard disk drive, an optical disc drive, or a portable memory device. As firmware, the logic may be stored in persistent storage.

Embodiments described herein are generally directed to a disinfection device capable of disinfecting the hubs of medical devices. For example, the disinfection device may be used to disinfect one or more hubs of a multi-lumen catheter, infusion catheter, port, or other medical device. In some aspects, the one or more hubs may include a male or female Luer connector.

The germicidal or biocidal effects of ultraviolet (UV) radiation have been known since the late 19th century. In recent years the use of UV radiation has gained broad acceptance in the fields of water and air purification and has found some limited use in food processing and medical device sterilization.

UV light consists of high energy photons which occupy the 200 to 400 nanometer wavelengths of the electromagnetic spectrum. This means that UV light emits slightly less energy than soft X-ray radiation (e.g., having photon energies of 100-1000 electron volt or eV), but significantly more than visible light. UV energy does not directly kill pathogens, but rather causes a photochemical reaction with the genetic structure which inhibits the ability of the pathogens to reproduce, therefore, in effect, killing the pathogen.

The amount of energy delivered by UV light is inversely proportional to its wavelength, therefore, the shorter the wavelength, the greater the energy produced. In general, the UV light portion of the spectrum is made up of three segments: UV-A (315-400 nm), used for sun-tanning lamps; UV-B (280-315 nm); and UV-C(200-280 nm). The UV-B and UV-C regions contain wavelengths with the best biocidal action. Studies have shown that the wavelengths most effective in killing microbes are between 250-265 nm.

Reference is now first made to FIG. 1 which illustrates a disinfecting device 100 for disinfecting at least a portion of a medical device. Disinfecting device 100 may include a housing 102. The housing 102 is configured to fit within a hand of a user. The housing 102 may include a button or switch 110 that may turn on or operate disinfecting device 100. Located within the housing 102 are a rechargeable power supply 114 and an ultraviolet light source 116. In some aspects, the rechargeable power supply 114 may include a battery, capacitor, or inductance coil. In some aspects, the housing 102 may be configured to connect with a cable, such as a USB cable via a port 117, to recharge the power supply 114. In some aspects, the rechargeable power supply 114 may be configured to wirelessly recharge, for example, by inductive charging.

In some aspects, information may be uploaded from or downloaded to the disinfecting device 100 via the port 117. In some aspects, the port 117 allows for connection to an external device, such as a CPU. In some aspects, the external device may be configured to retain information about the use of disinfecting device 100. For example, the external device may store information related to each medical device being disinfected, settings associated with disinfection during each disinfection routine, when each disinfection routine occurs, and any other desired parameter. In some aspects, the external device may include one or more ultrasound machine, imaging device, catheter placement device, hospital emergency medical record (EMR) connected medical device, communications device, reconfirmation system, respirator, and infusion system.

The housing 102 may also include one or more indicator 112 that may be used to indicate a status of the disinfecting device 100. The one or more indicator 112 may provide an indication of the operating status of the disinfecting device 100. For example, the one or more indicator 112 may be configured to illuminate when the device 100 has been powered on, signal that the ultraviolet light source 116 is operating, and flash when disinfection of an attached medical device is complete. While three indicators are shown, it is understood that more or less may be provided. The one or more indicator 112 may include visible light spectrum light emitting diodes having at least one color. In some aspects, the one or more indicator 112 may be configured to have more than one color. In some aspects, the one or more indicator 112 may indicate a level of disinfection of an attached medical device. In some instances, the one or more indicator 112 may blink to indicate a stage or level of disinfection for an attached medical device. In some aspects, the one or more indicator 112 may comprise two or more colors, wherein a color indicates a stage or level of disinfection for a medical device hub. For example, in some embodiments a red light indicates incomplete or unsatisfactory disinfection while a yellow light may indicate an intermediary or active process of disinfection for an attached hub. Further still, a green light may indicate a satisfactory or complete disinfection.

The one or more indicator 112 may further be programmed to blink or otherwise demonstrate a lighted pattern to further communicate a status of the disinfecting device 100. For example, the one or more indicator 112 may be programmed to demonstrate a lighted pattern to indicate a low battery. In some aspects, the one or more indicator 112 may further be programmed to demonstrate and error or mechanical malfunction. In some instances, the one or more indicator 112 may be programmed to indicate that disinfecting device 100 is ready to connect with at least a portion of a medical device. In place of the one or more indicator 112, information to a user may be provided by a display screen (not shown), such as a LCD screen, that displays operation times, disinfection status, battery levels, or other such status notifications.

In some aspects, the housing 102 may be formed of an easily cleanable material such that the disinfection device 100 may be cleaned between uses. In some aspects, the housing 102 may be formed of a germ free or microbe resistant material.

The disinfecting device 100 may include an ultraviolet light source 116 located within the housing 102. The ultraviolet light source 116 may take the form of one or more LED, SLED, or other ultraviolet light generating device. The ultraviolet light source 116 is capable of producing ultraviolet light or radiation in order to render any microorganisms within or around at least a portion of a medical device associated with an end cap 106 innocuous. In some aspects, ultraviolet light source 116 comprises a biocidal lamp. In some aspects, the ultraviolet light source 116 may include a UV light emitting diode having a peak of wavelength within the range of UV-C 200-280 nm (in some embodiments, 225-265 nm). As used herein, the term "ultraviolet source" is used to denote a lamp, a light-emitting diode (LED), a superluminescent diode (SLED), a laser, or another similar technology that is capable of emitting wavelengths in the range of about 100 nm-400 nm, and/or which are capable of killing pathogens.

In some instances, the UV-light source 116 can be configured to emit the UV light in a range from about 200 nm to about 280 nm, which generally corresponds to the so-called UV-C range; however, the UV-light source 116 need not be limited to the UV-C range. Indeed, the UV-light source 116 can be configured to emit UV light anywhere in the UV portion of the electromagnetic spectrum. In an example, the UV-light source 116 can be alternatively configured to emit the UV light in a range from about 280 nm to about 315 nm, which corresponds to the so-called UV-B range. In another example, the UV-light source 116 can be alternatively configured to emit the UV light in a range from about 315 nm to about 400 nm, which corresponds to the so-called UV-A range. In consideration of the UV-light source 116 being configured to emit the UV light in the UV-C range, the UV-light source 116 can be a low-pressure mercury lamp with an emission peak at, for example, 254 nm; an excimer lamp with an emission peak at, for example, 222 nm; a pulsed xenon lamp, or one or more LEDs, which LEDs can independently have emission peaks at, for example, 265, 273, or 280 nm.

A tube 104 includes a first end 103 that is connected or attached to the housing 102. The tube 104 may pass through a wall of housing 102 into the interior of housing 107. A second end 105 of the tube 104 is free of the housing 102 and is located away from the housing 102. An end cap 106 is located at the second end 105 of the tube 104. Ultraviolet light that is emitted from the ultraviolet light source 116 within the housing 102 is propagated through the tube 104 to the end cap 106 in order to disinfect at least a portion of a medical device affixed to, surrounded by, or otherwise associated with the end cap 106. The end cap 106 may take the form of a hub or other connecting device. In some aspects, the end cap 106 may include one or more Luer connector, barbed port, or clamp. In some aspects, the end cap 106 may include a treaded connection. In some aspects, the end cap 106 may be one of a plurality of end caps and may also include one or more bend or elbow.

In some aspects, the tube 104 may include a reflective material configured to reflect or aim the ultraviolet light emitted from the ultraviolet light source 116 to the end cap 106. In some embodiments, interior surface of the tube 104 may include a ultraviolet (e.g., UV-C) reflective material, or other materials with high UV reflective properties. Ultraviolet reflective material may be provided to retain and reflect any ultraviolet radiation emitted by ultraviolet light source 116 within the housing 102 and guide it towards the end cap 106 in order to disinfect a portion of a medical device connected to or associated with the end cap 106.

In some aspects, the tube 104 may include one or more light fibers to transmit light from the ultraviolet light source 116 to the end cap 106. In some aspects, the tube 104 may include a plurality of lumens. In such an arrangement a first lumen may be configured to transmit the ultraviolet light while another lumen is configured for propagating fluids from a first location to a second location. In some aspects the one or more light fibers may be optical fibers that include Bragg gratings in which the index of refraction within the core of the optical fibers changes along its length, in order to reflect certain wavelengths and transmit others. The one or more light fibers may extend within the end cap 106 and be configured to optimize targeted dispersion patterns. The one or more light fibers may be arranged in a different configurations to maximize ultraviolet light transmission to a portion of a medical device requiring sterilization.

As illustrated in FIG. 1, the end cap 106 may be attached to a first hub 108 of a medical device. The disinfecting device 100 may disinfect at least a portion of the first hub 108 that is attached to the end cap 106. After disinfecting the first hub 108, the disinfecting device 100 may be attached to a second hub 109 of a medical device to disinfect at least a portion of the second hub 109.

In some aspects, the disinfecting device 100 may include memory and be preprogrammed with exposure time and power settings to ensure disinfection for various medical devices. The disinfecting device 100 may include a processor 118 configured to control the ultraviolet light source 116 to operate at a desired power for a desired duration of time depending on what type of medical device is requiring cleaning. In some aspects, the disinfecting device 100 may recognize the type of medical device requiring cleaning upon connection to the end cap 106, and initiate a preset disinfection routine that applies the proper ultraviolet exposure to ensure disinfection.

In one aspect, the disinfecting device 100 may include a sensor, camera, a radio-frequency identification (RFID) reader, barcode scanner, transmitter, or transceiver to aid in the identification of a medical device in need of disinfection. In some aspects, the sensor, camera, barcode scanner, transmitter, or transceiver may allow for wireless communication between the end cap 106 and the processor 118. In some aspects, the sensor, camera, barcode scanner, transmitter, or transceiver may utilize a BLUETOOTH® protocol. For example, various medical devices may be provided with a bar code, barcode (e.g., a matrix barcode such as a "QR code"), an RFID tag, or other descriptive information that may be received by the disinfecting device 100 upon connection of the hub to the end cap 106. Once identified, the disinfecting device 100 may perform the proper preset disinfection routine. In such an arrangement, the functionality of the device 100 may be fully integrated into the end cap 106. That is, the device 100 may be able to operate solely by connection of the end cap 106 to a portion of a medical device without additional input by a user. In some instances, the identification of a medical device to be disinfected may be associated with a particular patient such that information surrounding the disinfecting process of the patient's medical device may be transmitted to and stored in the patient's medical record. Such may allow medical professionals to confirm regular disinfecting processes have taken place. Additionally, alerts may be preconfigured within a medical record system such that a medical professional is alerted at regular intervals to disinfect a particular patient's medical device. For example, an alert may indicate a particular patient, a particular medical device, a particular date, a particular disinfecting process, and/or a disinfecting device capable of providing the required disinfecting process. Of course, such alerts may include additional information (e.g., patient room number, attending medical professional, etc.) and may be "snoozed" or delayed based on various circumstances such as the patient's medical state or provision of fluids, medicine, or other treatment via the medical device to be disinfected.

The disinfecting device 100 may be configured to power on manually or automatically. In one aspect, the disinfecting device 100 may power up and begin delivering ultraviolet radiation to a medical device by actuating the button or switch 110. In another aspect, the disinfecting device 100 may be configured to automatically power up and begin a disinfection regimen upon attachment of a medical device to end cap 106. Conversely, the disinfecting device 100 may cease operation when a medical device is detached or removed from the end cap 106.

Figure 2:
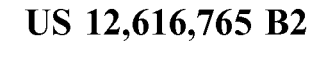
FIG. 2 illustrates a handheld disinfection device connected to a catheter requiring disinfection in accordance with an embodiment.

FIG. 2 illustrates a disinfecting device 100 being used to disinfect a connector 120 of a catheter 122. The end cap 106 may be configured to mate with connector 120 in order to transfer ultraviolet radiation from an ultraviolet source within housing 102 to the connector 120 in order to kill any potential pathogens or germs located on or in the connector 120. The catheter 122 may include any type of catheter configured to be placed in, or remove or input material from or into a body of a patient. For example, catheter 122 may be an infusion catheter, foley catheter, urine catheter, sensing catheter, or other type of catheter for placement on or in a patient.

Figure 3:
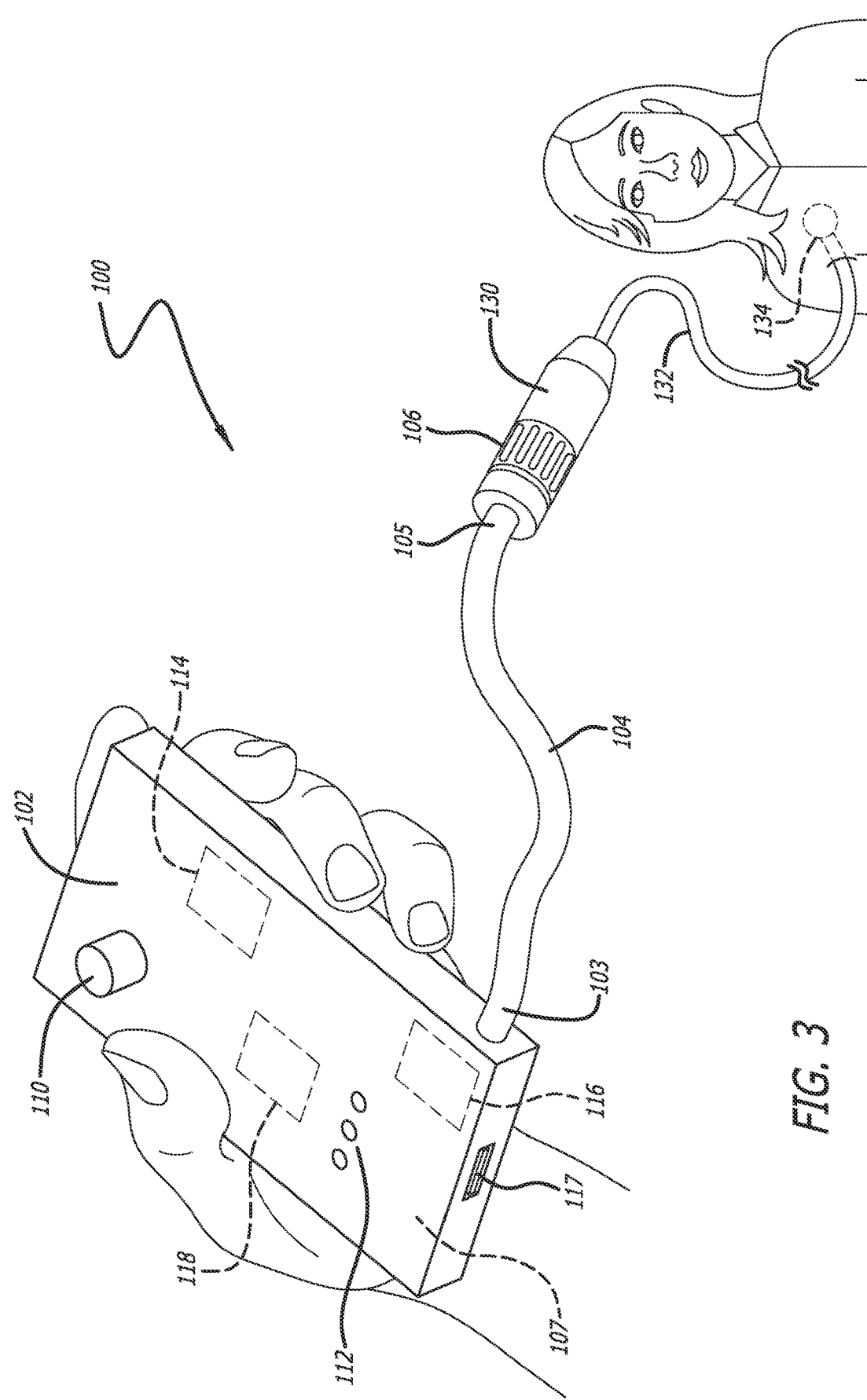
FIG. 3 illustrates a handheld disinfection device connected to a port requiring disinfection in accordance with an embodiment.

FIG. 3 illustrates a disinfecting device 100 being used to disinfect a connector 130 of a port 134. The end cap 106 is configured to mate with the connector 130 in order to transfer ultraviolet radiation from an ultraviolet source within housing 102 to the connector 130 in order to kill any potential pathogens or germs located on or in the connector 130. The port 134 may include any permanent or temporary port for accessing a patient's body.

Figure 4:
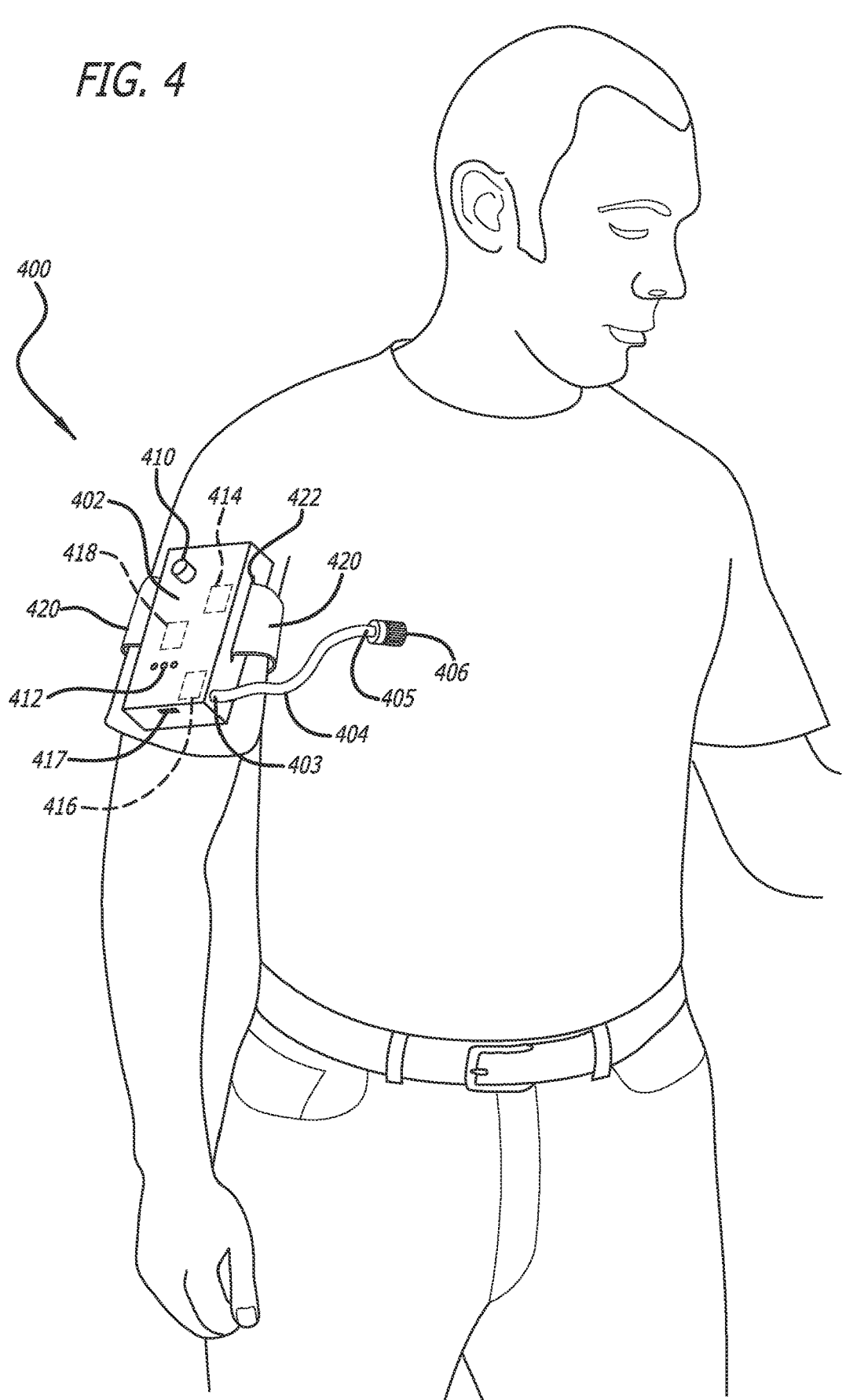
FIG. 4 illustrates a wearable disinfection device in accordance with an embodiment.

FIG. 4 illustrates a wearable disinfecting device 400 that may include features described above in relation to disinfecting device 100. The wearable disinfecting device 400 may include a housing 402. The housing 402 may be configured to be worn by a user. In some aspects, the housing 402 may be configured to attach to an appendage of a user such as a leg or arm. In some aspects, the housing 402 may be configured to attach to a garment worn by a user or be incorporated into a garment. The wearable disinfection device 400 allows a user's hands to remain free for other things.

The housing 402 may include a button or switch 410 that may turn on or operate disinfecting device 400. The housing 402 may also include one or more indicator 412 that may be used to indicate a status of the disinfecting device 400. The housing 402 may include a slot or recess 422 configured to anchor a belt or strap 420. The belt or strap 420 may be configured to surround an appendage in order to attach the housing 402 to the appendage.

The wearable disinfecting device 400 may include an ultraviolet light source 416 located within the housing 402. The ultraviolet light source 416 may take the form of any ultraviolet source as discussed above. A tube 404 includes a first end 403 that is connected or attached to the housing 402. In some aspects, the tube 404 may extend into the housing 402 to directly connect with the ultraviolet light source 416. A second end 405 of the tube 404 is free of the housing 402 and is located away from the housing 402. An end cap 406 is located at the second end 405 of the tube 404. Ultraviolet light that is emitted from the ultraviolet source within the housing 402 is propagated through the tube 404 to the end cap 406 in order to disinfect at least a portion of a medical device affixed to, surrounded by, or otherwise associated with the end cap 406. As with disinfecting device 100 discussed above, wearable disinfecting device 400 may include a port 417, processor 418, and rechargeable power supply 414.

FIG. 5A illustrates a disinfection system 500 that includes a medical device or medical network 502. In some aspects, the disinfection system 500 may be incorporated into a portion of a medical device or medical network 502. The disinfection system 500 may include a tube 504 that extends from the medical device or medical network 502 and ends with an end cap 506. An ultraviolet light source 516 associated with the medical device or medical network 502 may transmit radiation to the end cap 506 via the tube 504 to disinfect at least a portion of a medical device associated with the end cap 506.

In some aspects, the medical device or medical network 502 may include one or more ultrasound machine, imaging device, catheter placement device, hospital EMR, communications device, reconfirmation system, and infusion pump. In some aspects, the end cap 506 may be configured to receive power from one or more ultrasound machine, imaging device, catheter placement device, hospital EMR, communications device, reconfirmation system, and infusion pump.

In some aspects, the medical device or medical network 502 may include memory and be preprogrammed with exposure time and power settings to ensure disinfection for various medical devices. The medical device or medical network 502 may include a processor 518 configured to control the ultraviolet light source 516 to operate at a desired power for a desired duration of time depending on what type of medical device is requiring cleaning. In some aspects, the medical device or medical network 502 may recognize the type of medical device requiring cleaning upon connection to the end cap 506, and initiate a preset disinfection routine that applies the proper ultraviolet exposure to ensure disinfection.

In one aspect, the medical device or medical network 502 may include a sensor, camera, RFID reader, barcode scanner, transmitter, or transceiver to aid in the identification of a medical device in need of disinfection. In some aspects, the sensor, camera, barcode scanner, transmitter, or transceiver may allow for wireless communication between the end cap 506 and the processor 518. In some aspects, the sensor, camera, barcode scanner, transmitter, or transceiver may utilize a Bluetooth protocol. For example, various medical devices may be provided with a bar code, QR code, RFID tag, or other descriptive information that may be received by the medical device or medical network 502 upon connection of the hub to the end cap 506. Once identified, the medical device or medical network 502 may perform the proper preset disinfection routine.

The medical device or medical network 502 may be configured to store operational information. The medical device or medical network 502 may be configured to track treatment time and power associated with ultraviolet light transmission to a medical device associated with the end cap 506. Additionally, the medical device or medical network 502 may store and track timestamps associated with treatment routines, locations, medical devices cleaned, patients associated with each disinfected medical device, and other desired parameters.

In some aspects, disinfection of a medical device may be initiated manually or automatically. In one aspect, the medical device or medical network 502 may power up and begin delivering ultraviolet radiation to a medical device connected to the end cap 506 by actuating a button or switch. In another aspect, the medical device or medical network 502 may be configured to automatically power up and begin a disinfection regimen upon attachment of a medical device to the end cap 506. Conversely, the medical device or medical network 502 may cease operation when a medical device is detached or removed from the end cap 506.

FIG. 5B illustrates a disinfection system 500 including an infusion pump 510. Extending from infusion pump 510 is a tube 504 having an end cap 506. The end cap 506 is configured to connect to or receive at least a portion of a medical device requiring disinfection. As illustrated in FIG. 5B, a medical device includes a first hub 508 and a second hub 509. The end cap 506 is configured for connection with both first hub 508 and second hub 509 in order to guide ultraviolet light thereto.

Figure 6:
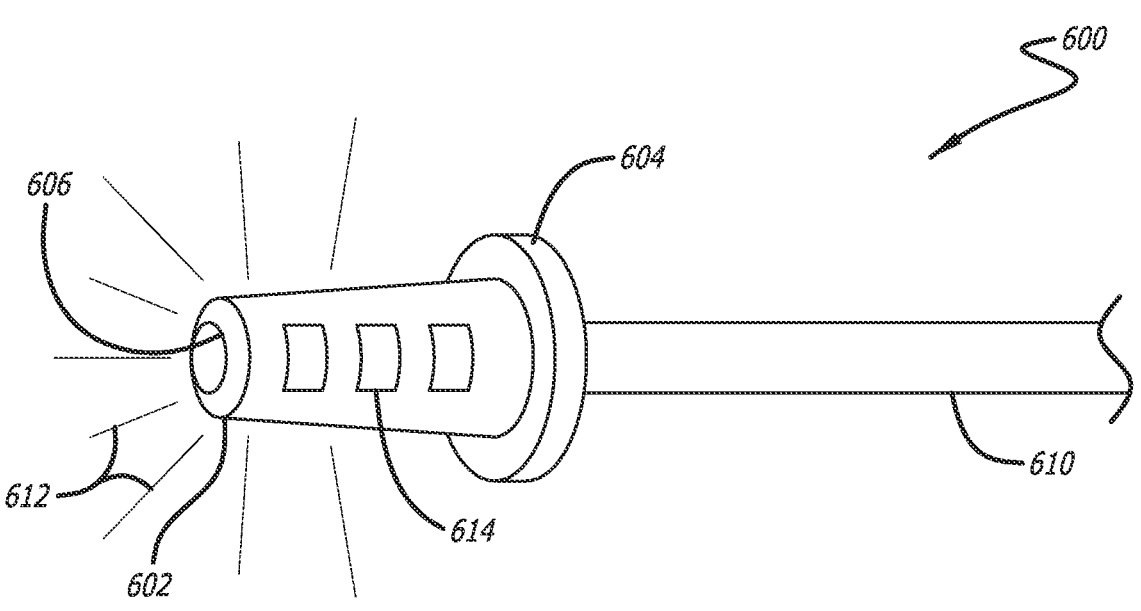
FIG. 6 illustrates a male end cap of the disinfection device in accordance with an embodiment.

FIG. 6 illustrates a male end cap 600 for use with a disinfection device in accordance with an embodiment. In some aspects, the male end cap 600 may take the form of a male Luer connector. The male end cap 600 is configured to attach to at least a portion of a medical device that requires disinfection. In some aspects, the portion of the medical device may include a hub, a connector, a catheter, or a port.

The male end cap 600 may include a proximal end 604 and a distal end 602. The male end cap 600 may include an outer surface that tapers from the proximal end 604 towards the distal end 602. The proximal end 604 of the male end cap 600 may be connected to a distal end of a tube 610 that is configured to propagate ultraviolet light from a source to the male end cap 600. The ultraviolet light may be contained in the male end cap 600 or may be configured to radiate from the male end cap 600 as indicated at 612 in order to clean and sanitize an inner surface of a portion of a medical device.

In some aspects, the male end cap 600 may be formed entirely of an ultraviolet transparent material. In other aspects, the male end cap 600 may be formed of an opaque material, but include one or more window 614 to allow ultraviolet light out. The male end cap 600 may include an inner surface 606 that includes an ultraviolet reflective material that guides the ultraviolet radiation to the one or more window 614. In some aspects, an inner surface of the tube 610 may be coated with reflective material. In other aspects, one or more optic fibers may be located in tube 610 to transmit the ultraviolet light from the source.

Figure 7:
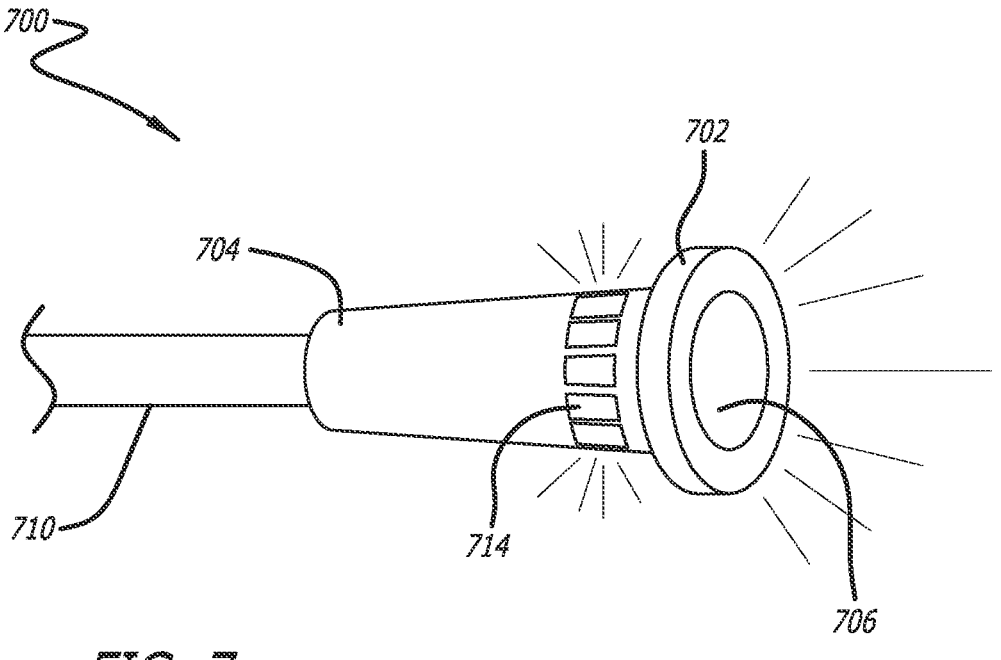
FIG. 7 illustrates a female end cap of the disinfection device in accordance with an embodiment.

FIG. 7 illustrates a female end cap 700 for use with a disinfection device in accordance with an embodiment. In some aspects, the female end cap 700 may take the form of a female Luer connector. The female end cap 700 is configured to attach to at least a portion of a medical device that requires disinfection. In some aspects, the portion of the medical device may include a hub, a connector, a catheter, or a port.

The female end cap 700 may include a proximal end 704 and an open distal end 702. The female end cap 700 may include an outer surface that tapers from the open distal end 702 towards the proximal end 704. The proximal end 704 of the female end cap 700 may be connected to a distal end of a tube 710 that is configured to propagate ultraviolet light from a source to the female end cap 700. In some aspects, the ultraviolet light may be contained in the female end cap 700. In other aspects, a portion of the ultraviolet light may be configured to radiate from the female end cap 700.

In some aspects, the female end cap 700 may be formed entirely of an ultraviolet transparent material. In other aspects, the female end cap 700 may be formed of an opaque material, but include one or more window 714 to allow ultraviolet light to escape. The female end cap 700 may include an inner surface 706 that includes an ultraviolet reflective material that reflects light to a portion of a medical device located within the female end cap 700. In some aspects, the reflective material may guide the ultraviolet radiation to the one or more window 714. In some aspects, an inner surface of the tube 710 may be coated with reflective material. In other aspects, one or more optic fibers may be located in tube 710 to transmit the ultraviolet light from the source.

Figures 8, 9:
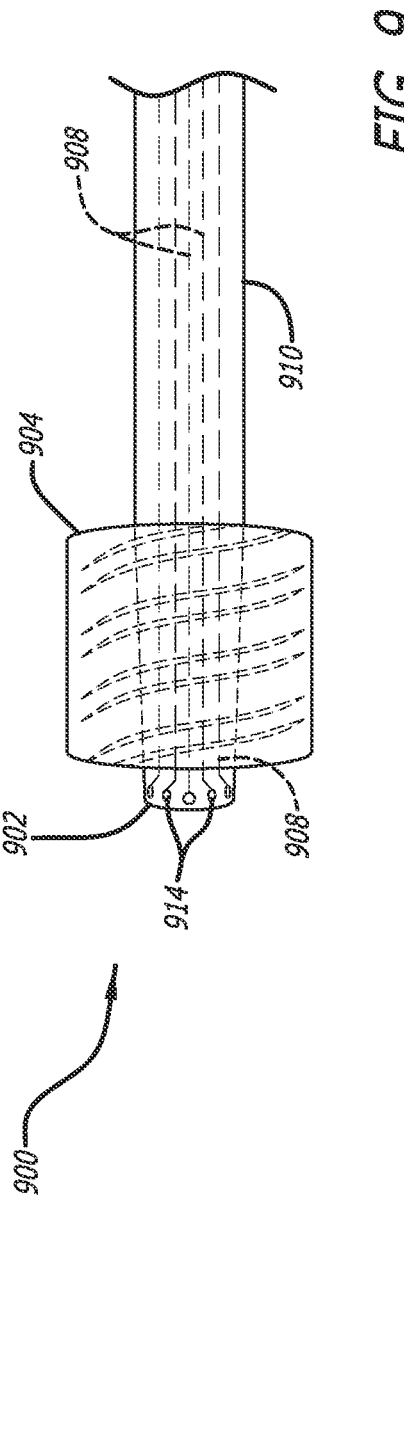
FIG. 8 illustrates a male end cap of the disinfection device in accordance with an embodiment.
FIG. 9 illustrates a male end cap of the disinfection device in accordance with an embodiment.

FIG. 8 illustrates a male end cap 800 for use with a disinfection device in accordance with an embodiment. In some aspects, the male end cap 800 may take the form of a male Luer connector. The male end cap 800 is configured to attach to at least a portion of a medical device that requires disinfection. In some aspects, the portion of the medical device may include a hub, a connector, a catheter, or a port.

The male end cap 800 may include a proximal end 804 and a distal end 802. The male end cap 800 may include an outer surface that tapers from the proximal end 804 towards the distal end 802. The proximal end 804 of the male end cap

800 may be connected to a distal end of a tube 810 that is configured to propagate ultraviolet light from a source to the male end cap 800. The ultraviolet light may be contained in the male end cap 800 or may be configured to radiate from the male end cap 800 to clean and sanitize an inner surface of a portion of a medical device.

The male end cap 800 may be formed of an ultraviolet transparent material which allows light carried by integrated light fibers 808 to be released. In some aspects, the light fibers 808 may extend through the tube 810 to the ultraviolet light source. The light fibers 808 may end in one or more window 814 to allow for directing of ultraviolet light to specific locations of an attached medical device requiring cleaning or sterilizing. The one or more window 814 may be formed at termination points for the light fibers 808 or may include one or more lens.

FIG. 9 illustrates a female end cap 900 for use with a disinfection device in accordance with an embodiment. In some aspects, the female end cap 900 may take the form of a female Luer connector. The female end cap 900 is configured to attach to at least a portion of a medical device that requires disinfection. In some aspects, the portion of the medical device may include a hub, a connector, a catheter, or a port.

The female end cap 900 may include a proximal end 904 and an open distal end 902. The female end cap 900 may include an outer surface that tapers from the open distal end 902 towards the proximal end 904. The proximal end 904 of the female end cap 900 may be connected to a distal end of a tube 910 that is configured to propagate ultraviolet light from a source to the female end cap 900. In some aspects, the ultraviolet light may be contained in the female end cap 900. In other aspects, a portion of the ultraviolet light may be configured to radiate from the female end cap 900.

The female end cap 900 may be formed of an ultraviolet transparent material which allows light carried by integrated light fibers 908 to be released. In some aspects, the light fibers 908 may extend through the tube 910 to the ultraviolet light source. The light fibers 908 may end in one or more window 914 to allow for directing of ultraviolet light to specific locations of an attached medical device requiring cleaning or sterilizing. In some aspects, the one or more window 914 may be located within the female end cap 900. The one or more window 914 may be formed at termination points for the light fibers 908 and may include one or more lens.

It should therefore be understood that these and other variations of the principles described herein are contemplated and that the cross-sectional profiles of the multi-lumen catheter tubes disclosed herein can vary as appreciated by one skilled in the art.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A disinfecting device, comprising:
a housing;
an ultraviolet source located in the housing;
a tube that includes a first end connected to the housing and a second end free of the housing; and
an end cap located at the second end of the tube, wherein ultraviolet light is emitted from the ultraviolet source and propagated to the end cap,
wherein the tube includes a first lumen configured to transmit the ultraviolet light and a second lumen configured to propagate a fluid from a first location to a second location.

2. The disinfecting device of claim 1, wherein the tube or the end cap includes a reflective material coating configured to propagate the ultraviolet light.

3. The disinfecting device of claim 2, wherein the reflective material coating is positioned on an inner surface of the tube or the end cap.

4. The disinfecting device of claim 2, wherein the reflective material coating is positioned on an outer surface of the tube or the end cap.

5. The disinfecting device of claim 1, wherein the tube or the end cap includes one or more optical fibers configured to transmit the ultraviolet light.

6. The disinfecting device of claim 5, wherein the one or more optical fibers is embedded in a wall of the tube or the end cap.

7. The disinfecting device of claim 1, wherein the ultraviolet source includes one or more light emitting diodes (LEDs) or superluminescent diodes (SLEDs).

8. The disinfecting device of claim 1, wherein the housing is configured to be held in a hand of a user.

9. The disinfecting device of claim 1, wherein the housing includes a strap configured to be placed around an extremity of a user resulting in the user wearing the disinfecting device.

10. The disinfecting device of claim 1, further comprising a pump located within the housing.

11. The disinfecting device of claim 10, wherein the pump is an infusion pump.

12. The disinfecting device of claim 1, wherein the end cap is configured to attached to a medical device.

13. The disinfecting device of claim 12, wherein the medical device is one or more of a hub, a catheter, and a port.

14. The disinfecting device of claim 1, wherein the end cap is a Luer connector.

15. The disinfecting device of claim 1, wherein the end cap is a barbed port.

16. The disinfecting device of claim 1, wherein the end cap includes a friction fit connector.

17. The disinfecting device of claim 1, further comprising:
a power source configured for providing power to the ultraviolet source.

18. The disinfecting device of claim 17, wherein the power source is one or more of a battery, a capacitor, or an inductance coil.

19. The disinfecting device of claim 1, further comprising a transmitter or a transceiver configured to receive a program indicating a disinfecting process to be performed.

20. The disinfecting device of claim 19, wherein the transmitter or the transceiver includes a radio-frequency identification (RFID) or wireless-communication enabled transmitter or transceiver.

* * * * *